(12) United States Patent
Leino et al.

(10) Patent No.: US 6,277,778 B1
(45) Date of Patent: Aug. 21, 2001

(54) HETEROATOM SUBSTITUTED METALLOCENE COMPOUNDS FOR OLEFIN POLYMERIZATION CATALYST SYSTEMS AND METHODS FOR PREPARING THEM

(75) Inventors: Reko Leino, Turku; Hendrik Luttikhedde, Nousiainen; Carl-Erik Wilen; Jan Näsman, both of Turku, all of (FI)

(73) Assignee: Borealis A/S, Lyngby (DK)

( * ) Notice: Subject to any disclaimer, the term of this patent is extended or adjusted under 35 U.S.C. 154(b) by 0 days.

(21) Appl. No.: 09/117,439

(22) PCT Filed: Jan. 30, 1997

(86) PCT No.: PCT/FI97/00049

§ 371 Date: Sep. 23, 1998

§ 102(e) Date: Sep. 23, 1998

(87) PCT Pub. No.: WO97/28170

PCT Pub. Date: Aug. 7, 1997

(30) Foreign Application Priority Data

Jan. 30, 1996 (FI) .......................................... 960437

(51) Int. Cl.⁷ ................ B01J 21/00; B01J 21/06
(52) U.S. Cl. ................ 502/117; 502/103; 502/152; 526/160; 556/53
(58) Field of Search ................... 502/117, 103, 502/152; 556/53; 526/160

(56) References Cited

U.S. PATENT DOCUMENTS

| 5,166,216 | 11/1992 | Schuetz et al. ................ 514/406 |
| 5,635,437 | * 6/1997 | Burkhardt et al. ............... 502/104 |
| 6,140,521 | * 10/2000 | Chen et al. ..................... 556/27 |

FOREIGN PATENT DOCUMENTS

| 0485822A2 | 5/1992 | (EP) ......................... 4/602 |
| 0584609A2 | 3/1994 | (EP) ......................... 4/602 |
| 94 28034 | 12/1994 | (WO) ........................ 4/602 |
| 96 00243 | 1/1996 | (WO) ........................ 4/642 |
| 97 28170 | 8/1997 | (WO) . |

OTHER PUBLICATIONS

Organometallics 1996, 2540–2453, Isospecific Propylene Polymerization with a Novel 2–Substituted Bis(indenyl) ansa–Zirconcene, Reko Leino et al, May.

\* cited by examiner

Primary Examiner—Mark L. Bell
Assistant Examiner—Michael J. DiVerdi
(74) Attorney, Agent, or Firm—Birch, Stewart, Kolasch & Birch, LLP (57) ABSTRACT

According to the invention a new catalyst precursor is obtained, in which alkoxy or siloxy substitution in the 2-position of 5-membered ring of indenyl compound has been carried out. Thereby a metallocene compound is achieved, in which an oxygen atom is directly bonded to the 2-position of a pentahapto indenyl moiety. The catalyst precursors can be used as components for olefin polymerization catalysts.

12 Claims, 1 Drawing Sheet

Figure 1  Comparison of the effect of siloxysubstitution on the activity of the metal centre

HETEROATOM SUBSTITUTED METALLOCENE COMPOUNDS FOR OLEFIN POLYMERIZATION CATALYST SYSTEMS AND METHODS FOR PREPARING THEM

This application is the national phase under 35 U.S.C. §371 of prior PCT International Application No., PCT/JP97/03908, which has an International filing date of Jan. 30, 1997, which designated the United States of America, the entire contents of which are hereby incorporated by reference.

The present invention relates to novel metallocene catalyst systems for homo- and copolymerization of olefins, especially propylene, ethylene and higher alpha-olefins, in the presence of a cocatalyst, such as methylaluminoxane (MAO). Especially the invention relates to metallocenes with heteroatom substituted indenyl and indenyl derivative ligands, a method for their preparation, and their use in polymerization of olefins, especially propylene and ethylene.

Chiral $C_2$ symmetric bis(indenyl)ansa-metallocenes are precursors to highly active catalysts for stereoselective polymerization of alpha-olefins. The performance characteristics of these systems are different, the variations being induced by size and position of the substituents. E.g., dimethylsilylene bridged 2,2'-dimethyl-4,4'-diaryl substituted bis(indenyl)zirconocenes developed by Brintzinger and co-workers (Organometallics 1994, 13, 964) and Spaleck et al. (Organometallics 1994, 13, 954), produce isotactic polypropylenes with catalyst activities and polymer properties comparable to those obtained with heterogeneous Ziegler-Natta catalysts.

The area of electronically altered bis(indenyl) metallocenes has remained relatively unexplored. Previously, it has been reported that halogen or alkoxy substitution in the six-membered rings of indenes reduces the activity of the catalyst system and the molecular weight of the produced polymer (Consiglio et al, Organometallics 1990, 9, 3098; Collins et al., Organometallics 1992, 11, 2115). Bis(indenyl) zirconocenes with 2-amino functionalized ligands have been reported recently by several groups (Luttikhedde et a/., Organometallics 1996, 15, 3092; Plenio and Burth, J. Organomet Chem. 1996, 519, 269; Brintzinger et al., J. Organomet. Chem. 1996, 520, 63). The bridged complexes show somewhat lower catalytic activities compared with their unsubstituted bis(indenyl)zirconocene analogues.

The present invention concerns novel metallocene complexes (I) with an oxygen atom directly bonded to the 2-position of a pentahapto indenyl moiety, e.g., racemic [ethylenebis(2-(tert-butyldimethylsiloxy)indenyl)] zirconium dichloride, and their application in polymerization of olefins. These complexes (I), in combination with MAO or other activators, form highly active catalyst systems for homo- and copolymerization of olefins. E.g., the I/MAO catalyst systems polymerizes propylene to highly isotactic polypropylene. The propylene and ethylene polymerization activities of these (I)/MAO systems exceeds those of several conventional ansa-metallocene/MAO catalyst systems, such as dimethylsilylenebis(4,5,6,7-tetrahydroindenyl)zirconium dichloride/MAO, under similar polymerization conditions. The novel catalyst systems are very stable and retain their high activities at exceptionally low [Al]:[Zr] ratios.

According to the invention a new catalyst precursor is obtained, in which a siloxy substitution in the 2-position of 5-membered ring of an indenyl-type compound has been carried out. Thereby it is possible to produce metallocene compounds, in which an oxygen atom is directly bonded to the 2-position of a penta-hapto indenyl moiety.

Thus the catalyst precursor according to the invention concerns an indenyl compound having the formula (I):

wherein: each IndY is the same or different and is one of a mono- or polysubstituted, fused or non-fused, homo- or heterocyclic indenyl ligand, dihydroindenyl ligand or tetrahydroindenyl ligand, which ligand is substituted at the 2-position of its indenyl structure by the group Y, which group Y has the following structure (II):

(II)

$$\text{—O—}\underset{\underset{R^{3'}}{|}}{\overset{\overset{R^{3}}{|}}{D}}\text{—}R^{4}$$

wherein D is one of silicon or germanium, $R^3$, $R^{3'}$ and $R^4$ are the same or different and are one of a hydrogen atom, a $C_1$–$C_{10}$ hydrocarbyl group or a $C_1$–$C_{10}$ hydrocarbyloxy group, or at least two of $R^3$, $R^{3'}$ and $R^4$ form together a $C_2$–$C_{20}$ ring structure; M is a transition metal of group 4 of the Periodic Table and is bound to the ligand IndY in at least an $\eta_5$ bonding mode; each R is the same or different and is one of a hydrogen atom, a halogen atom, a $C_1$–$C_{10}$ hydrocarbyl group, a $C_1$–$C_{10}$ hydrocarbyloxy group, a tri-hydrocarbyl silyl group or two R form together a $C_2$–$C_{20}$ ring structure; B is a bridge atom or group between two IndY ligands or between one IndY ligand and the transition metal M; m is 1 or 2; o is 0 or 1; and n is 4–m when there is no bridge B or B is a bridge atom or group between two IndY ligands, or n is 4–m–o when B is a bridge atom or group between one IndY ligand and the transition metal M.

By mono- or polysubstituted is meant that, in addition to said substituent Y, there may optionally be other substituents at the rings at said ligand IndY.

By fused or non-fused is meant that any ring at said ligand IndY may be fused or non-fused, i.e. have at least two atoms in common, with at least one further ring.

By homo- and heterocyclic is meant that any ring of said ligand IndY may have only carbon ring atoms (homo- or isocyclic) or may have other ring atoms than carbon (heterocyclic).

Preturately the indenyl compound according to formula (I) has the following formula (III)

where
M is a metal selected from zirconium, titanium or hafnium,
D is an element selected from silicon (Si) or germanium (Ge), B is a bridge comprising at least one of —(CH$_2$)$_n$—, —Si(R$_3$)$_2$— or —Ge(R$_3$)$_2$—, R$^1$ and R$^2$ are the same or different groups selected from a hydrogen atom, a C$_1$–C$_{10}$ alkyl group, C$_1$–C$_{10}$ alkoxy group, C$_6$–C$_{10}$ aryl group, C$_6$–C$_{10}$ aryloxy group, C$_2$–C$_{10}$ alkenyl group, C$_2$–C$_{10}$ arylalkyl group, C$_2$–C$_{10}$ alkylaryl group, C$_8$–C$_{40}$ arylalkenyl group or a halogen atom, preferably a C$_1$–C$_{10}$ alkyl group and/or a halogen atom.

R$^{3'}$, R$^3$–R$^6$ are same or different groups selected from hydrogen, C$_1$–C$_{10}$ alkyl group, C$_1$–C$_{10}$ alkoxy group, C$_6$–C$_{10}$ aryl group, C$_6$–C$_{10}$ aryloxy group, C$_2$–C$_{10}$ alkenyl group, C$_2$–C$_{10}$ arylalkyl group, C$_2$–C$_{10}$ alkylaryl group, C$_8$–C$_{40}$ arylalkenyl group and a halogen atom. R$^3$ and R$^{3'}$ groups can also be connected to each other to form a ring structure and R$_4$ may also be part of a ring structure.

Preferably M$_1$ is zirconium.

R$^1$ and R$^2$ are preferably the same and most preferably they are halogen atoms, for example chlorine atoms.

R$^3$ is preferably C$_1$–C$_{10}$ alkyl or aryl group and most preferably it is methyl group. R$^4$ is likewise preferably C$_1$–C$_{10}$ alkyl or aryl group, for example tert-butyl group, t-hexyl group or cyclohexyl group.

Most preferably D is Si, B is —CH$_2$CH$_2$—, R$^1$=R$^2$ and is chlorine, R$^3$ is CH$_3$ and R$^5$–R$^6$ is aromatic or fused aromatic or alkyl or hydrogen.

The invention also relates to 2-trihydrocarbyl and 2-trihydrokarbyloxy siloxyindene and germyloxyindene compounds having the general formula:

(IV)

wherein: D is one of silicon and germanium; R$^3$, R$^{3'}$ and R$^4$ are the same or different and are one of a hydrogen atom, a C$_1$–C$_{10}$ hydrocarbyl group or a C$_1$–C$_{10}$ hydrocarbyloxy group, or at least two of R$^3$, R$^{3'}$ and R$^4$ form together a C$_2$–C$_{20}$ ring structure; R$^7$ is a four-atom chain forming an unsubstituted or substituted, further non-fused or further fused, homocyclic (=isocyclic) or heterocyclic, unsaturated or saturated, aliphatic or aromatic six-membered ring; and R$^8$, R$^9$ and R$^{10}$ are the same or different and are one of a hydrogen atom, a C$_1$–C$_{10}$ hydrocarbyl group, a C$_1$–C$_{10}$ hydrocarbyloxy group, a tri-C$_1$–C$_{10}$ hydrocarbyl silyl group or a tri-C$_1$–C$_{10}$ hydrocarbyloxy silyl group, or one of R$^8$ and R$^9$ may be a bridge atom or group B to a cyclopentadienyl, fluorenyl or indenyl group. Preferably, they have the formula:

(V)

wherein: R$^{3'}$, R$^3$–R$^6$ are the same or different and are one of a hydrogen atom, a C$_1$–C$_{10}$ alkyl group, a C$_1$–C$_{10}$ alkoxy group, a C$_6$–C$_{10}$ aryl group, a C$_2$–C$_{10}$ alkenyl group, a C$_7$–C$_{22}$ arylalkyl group, a C$_7$–C$_{22}$ alkylaryl group, a C$_8$–C$_{23}$ arylalkenyl group or a halogen atom, or at least two of R$^3$, R$^{3'}$ and R$^4$ form together a C$_2$–C$_{10}$ ring structure, and R$^8$, R$^9$ and R$^{10}$ are the same as above, alternatively, or the formula:

(VI)

wherein: R$^3$, R$^{3'}$, R$^4$–R$^6$, R$^8$, R$^{10}$ and D are the same as above; and B is a bridge of at least one of the groups —(CH$_2$)$_n$—, —SiR$^3$$_2$—, or —GeR$^3$$_2$—, wherein n is 1–8 and R$^3$ is the same as above. D is preferably Si.

The catalyst compounds according to the invention can be prepared from 2-indanone. This compound can be reacted in a suitable solvent with a base and a chlorosilane to form 2-siloxyindene with a yield of over 80%. Suitable solvents are for example dimethylformamide (DMF) and tetrahydrofurane (THF). Suitable bases are for example imidazole, triethylamine (TEA) and 1,8-diazabicyclo[5.4.0]undec-7-ene. Suitable chlorosilanes are for example tert-butyldimethylchlorosilane, t-hexyldimethylchlorosilane and cyclohexyldimethylchlorosilane. The reaction takes place according to the following reaction scheme (VII):

(VII)

According to one embodiment of the invention 2-(tert-butyldimethylsiloxy)indene is reacted first with butyllithium and then with dimethyl dichlorosilane (Me$_2$SiCl$_2$) to form dimethylsilylbis(2-(tert-butyldimethylsiloxy)indenyl)silane. Butyllithium can be replaced with methyllithium, sodium hydride or potassium hydride. Likewise dimethyl dichlorosilane can be replaced with any dialkyl or diarylsilane. Silicon can be replaced with germanium.

Dimethylsilylbis(2-(tert-butyldimethylsiloxy)indenyl)silane can be reacted with butyllithium, which gives the corresponding bislithium salt. This product can be reacted with zirconium tetrachloride to yield [dimethylsilylbis(2-

(tert-butyldimethylsiloxy)indenyl)]zirconium dichloride as a mixture of the racemic and meso diastereomers. Butyllithium may be replaced as described earlier. Zirconium tetrachloride can be replaced with titanium tetrachloride or hafnium tetrachloride to give the corresponding titanium and hafnium complexes. The reactions take place according to the following reaction schemes (VIII and IX):

(VIII)

+

(IX)

According to another embodiment of the invention 2-(tert-butyldimethylsiloxy)indene is reacted first with butyllithium and then with dibromoethane to form bis(2-(tert-butyldimethylsiloxy)indenyl)ethane. This compound can be reacted with two equivalents of butyllithium, which gives the corresponding bislithium salt. This can then be reacted with zirconium tetrachloride to yield [ethylenebis(2-(tert-butyldimethylsiloxy)indenyl)]zirconium dichloride. The racemic diastereomer of the latter is formed in great excess and is easily separated from the meso isomer by fractional crystallization. Catalytic hydrogenation of racemic [ethylenebis(2-(tert-butyldimethylsiloxy)indenyl)] zirconium dichloride yields the corresponding tetrahydroindenyl complex. The reactions take place according to the following reaction scheme (X):

In the reactions above butyllithium may be replaced as described earlier. Zirconium tetrachloride can be replaced with titanium tetrachloride or hafnium tetrachloride to give the corresponding titanium and hafnium complexes.

According to still another embodiment of the invention 2-(t-hexyldimethylsiloxy)indene is reacted first with butyllithium and then with dibromoethane to form bis(2-(t-hexyldimethylsiloxy)indenyl)ethane. This compound can be reacted with two equivalents of butyllithium which gives the corresponding bislithium salt. This can then be reacted with with zirconium tetrachloride to yield [ethylenebis(2-(t-hexyldimethylsiloxy)indenyl)]zirconium dichloride. The racemic diastereomer of the latter is formed in great excess and is easily separated from the meso isomer by fractional crystallization. The reactions take place according to the following reaction scheme (XI):

In the reactions above butyllithium may be replaced as described earlier. Zirconium tetrachloride can be replaced with titanium tetrachloride or hafnium tetrachloride to give the corresponding titanium and hafnium complexes. Hydrogenation of [ethylenebis(2-(thexyldimethylsiloxy)indenyl)] zirconium dichloride yields the corresponding tetrahydroindenyl complex.

Illustrative but non-limiting examples of the compounds according to the invention are, among others, 2-(tert-butyldimethylsiloxy)indene, 2-(t-hexyldimethylsiloxy) indene, 2-(cyclohexyldimethyl-siloxy)indene, 2-(tert-butyldiphenylsiloxy)indene, dimethylsilylbis(2-(tert-butyldimethylsiloxy)indene), diphenylsilylbis(2-(tert-butyldimethylsiloxy)indene), dimethylsilylbis(2-(thexyldimethylsiloxy)indene), diphenylsilylbis(2-(thexyldimethylsiloxy)indene), dimethylsilylbis(2-(cyclohexyldimethylsiloxy)indene), diphenylsilylbis(2-(cyclohexyldimethylsiloxy)indene), dimethylsilylbis(2-(tert-butyldiphenylsiloxy)indene), diphenylsilylbis(2-(tert-butyldiphenylsiloxy)indene), racemic and meso [dimethylsilylbis(2-(tert-butyldimethylsiloxy)indenyl)] zirconium dichloride, racemic and meso[diphenylsilylbis(2-(tert-butyldimethylsiloxy)indenyl)]zirconium dichloride, racemic and meso[dimethylsilylbis(2-(t-hexyldimethylsiloxy)indenyl)]zirconium dichloride, racemic and meso[diphenylsilylbis(2-(t-hexyldimethylsiloxy) indenyl)]zirconium dichloride, racemic and meso [dimethylsilylbis(2-(cyclohexyldimethylsiloxy)indenyl)] zirconium dichloride, racemic and meso[dimethylsilylbis(2-(cyclohexyldimethylsiloxy)indenyl)]zirconium dichloride, racemic and meso[dimethylsilylbis(2-2-(tert-butyldiphenylsiloxy)indenyl)]zirconium dichloride, racemic and meso[diphenylsilylbis(2-(tert-butyldiphenylsiloxy) indenyl)]zirconium dichloride, racemic and meso [dimethylsilylbis(2-(tert-butyldimethylsiloxy)-4,5,6,7-tetrahydroindenyl)]zirconium dichloride, racemic and meso [diphenylsilylbis(2-(tert-butyldimethylsiloxy)-4,5,6,7-tetrahydroindenyl)]zirconium dichloride, racemic and meso [dimethylsilylbis(2-(thexyldimethylsiloxy)-4,5,6,7-tetrahydroindenyl)]zirconium dichloride, racemic and meso [diphenylsilylbis(2-(t-hexyldimethyl-siloxy)-4,5,6,7tetrahydroindenyl)]zirconium dichloride, racemic and meso[dimethylsilylbis(2-(cyclohexyldimethylsiloxy)-4,5,6,7-tetrahydroindenyl)]zirconium dichloride, racemic and meso[diphenylsilylbis(2-(cyclohexyldimethylsiloxy)-4,5,6,7-tetrahydroindenyl)]zirconium dichloride, racemic and meso[dimethylsilylbis(2-(tert-butyldiphenylsiloxy)-4,5,6,7-tetrahydroindenyl)]zirconium dichloride, racemic and meso [diphenylsilylbis(2-(tert-butyldiphenylsiloxy)-4,5,6,7-tetrahydroindenyl)]-zirconium dichloride, bis(2-(tert-butyldimethylsiloxy)indenyl)ethane, bis(2-(thexyldimethylsiloxy)indenyl)ethane, bis(2-(tert-butyldiphenylsiloxy)indenyl)ethane, bis(2-(cyclohexyldimethylsiloxy)indenyl)ethane, [rac-ethylenebis (2-(tert-butyldimethylsiloxy)indenyl)]zirconium dichloride, racemic and meso[ethylenebis(2-(t-hexyldimethylsiloxy) indenyl)]zirconium dichloride, racemic and meso [ethylenebis(2-(cyclohexyldimethylsiloxy)indenyl)] zirconium dichloride, racemic and meso[ethylenebis(2-(tert-butyldiphenylsiloxy)indenyl)]zirconium dichloride, [racethylenebis(2-(tert-butyldimethylsiloxy)-4,5,6,7-tetrahydroindenyl)]zirconium dichloride, racemic and meso [ethylenebis(2-(cyclohexyldimethylsiloxy)-4,5,6,7-tetrahydroindenyl)]zirconium dichloride, racemic and meso [ethylenebis(2-(tert-butyldiphenylsiloxy)-4,5,6,7-tetrahydroindenyl)]zirconium dichloride, bis(2-(t-hexyldimethylsiloxy)indenyl)ethane and [rac-ethylenebis(2-(t-hexyldimethylsiloxy)indenyl)]zirconium dichloride. Titanium or hafnium can be used instead of zirconium in corresponding complexes.

The metallocene compounds according to the invention can be used as catalyst components for polymerization or copolymerization of olefins. The olefins can be chosen from ethylene, propylene, butene, pentene, hexene, heptene and octene or mixtures thereof. Particularly the olefins can be selected from ethylene and propylene and mixtures thereof or together with other α-olefins.

The catalysts can be either unsupported or supported. The supported catalysts are mainly used for slurry and gas phase processes. The support can be any support known for metallocene and other type catalysts. Preferable supports are silica and alumina.

The compounds according to the invention can be used in combination with activator compounds, which are organometal compounds or any other compounds used in combination with metallocene compounds. Suitable cocatalysts are, for example, alkylalumininum compounds, aluminoxanes, methylaluminoxane, or modified methylaluminoxane. Preferred cocatalyst is methylaluminoxane (MAO). Other cocatalysts which may be used include Lewis or prolic acids, such as $(B(C_6F_5)_3$ or $[PhNMe_2H]^1B(C_6F_5)_4$, which generate cationic metallocenes with compatible non-coordinating anions in the presence or absence of alkylaluminum compounds. Especially suitable activators are, for example, alumoxane compounds having the formula of R—(Al(R)—O)$_m$—AlR$_2$ where n is 1–40, m is 3–40 and R is $C_1$–$C_8$ alkyl group. Preferably R is methyl group and the preferable activator is methylalumoxane (MAO). The activator can be applied according to the methods known in the art.

Experimental

All operations were carried out in argon or nitrogen atmosphere using standard Schlenk, vacuum or glove box techniques. Solvents used were dried and distilled under argon prior to use. The $^1$H- and $^{13}$C NMR spectra were recorded in CDCl$_3$ or CD$_2$Cl$_2$ solution using JEOL JNM-LA400 or Jeol JNM-A500 NMR spectro-meter and referenced against tetramethylsilane (TMS) or the residual protons of the deuterated solvents. Direct electron ionization mass spectra (EIMS) were obtained on a Varian VG-7070E or a Varian-8000 mass spectrometer.

Catalyst Preparation

EXAMPLE 1
2-(tert-butldimethylsiloxy)indene

A solution of tert-butyldimethylchlorosilane (248.69 g, 1.65 mol) and imidazole (112.33 g, 1.65 mol) in DMF (900 mL) was reacted with 2-indanone (198.24 g, 1.50 mol) and then stirred overnight at room temperature. The reaction mixture was treated with water (800 mL) and extracted with diethyl ether (3×400 mL). The combined organic phases were washed with water (2×400 mL) and dried over sodium sulfate. The solvents were removed under reduced pressure to leave an orange oil. Distillation under reduced pressure gave 331.2 g (89.6%) of the title compound as a yellow oil (bp 105–107° C./0.1 mbar). $^1$H NMR (CDCl$_3$, δ): 7.19–7.07 (m, 3H); 6.97 (td, $^3$J=7.3 Hz, $^4$J=1.4 Hz, 1H); 5.72 (dd, $^4$J=1.9 Hz, 1.1 Hz, 1H); 3.24 (dd, $^4$J=1.7 Hz, 1.1 Hz, 2H); 0.96 (s, 9H); 0.23 (s, 6H). $^{13}$C NMR (CDCl$_3$, δ): 162.44; 145.14; 136.53; 126.44; 123.01; 122.39; 118.92; 106.58; 39.46; 25.59; 18.14; −4.68.

EXAMPLE 2
2-(t-hexyldimethylsiloxy)indene

A solution of thexyldimethylchlorosilane (100.0 g, 559.3 mmol) and imidazole (38.08 g, 559.3 mmol) in DMF (350 mL) was reacted with 2-indanone (67.40 g, 510.0 mmol) and then stirred for two days at room temperature. The reaction mixture was treated with water (300 mL). and extracted with Et$_2$O (3×200 mL). The combined organic phases were washed with water (2×200 mL) and dried over sodium sulfate. Evaporation of the solvents left a red oil. Distillation under reduced pressure gave 116.89 g (83.5%) of the title compound as a yellow oil (bp. 128–130° C./0.4 mbar). $^1$H NMR (CDCl$_3$, δ): 7.24–7.10 (m, 3H); 7.00 (td, $^3$J=7.3 Hz, $^4$J=1.3 Hz, 1H); 5.74 (d, $^4$J=0.6 Hz, 1H); 3.28 (s, 2H); 1.70 (sept, $^3$J=6.8 Hz, 1H); 0.93 (s, 6H); 0.92 (d, $^3$J=6.8 Hz, 6H); 0.29 (s, 6H). $^{13}$C NMR (CDCl$_3$, δ): 162.82; 145.71; 137.03; 126.86; 123.45; 122.73; 119.29; 106.92; 40.00; 34.49; 25.51; 20.51; 18.89; −2.26.

EXAMPLE 3
2-(cyclohexyldimethylsiloxy)indene

A solution of cyclohexyldimethylchlorosilane (84.62 g, 478.7 mmol) and imidazole (32.59 g, 478.7 mmol) in DMF (300 mL) was reacted with 2-indanone (57.62 g, 436.0 mmol). The reaction mixture was stirred overnight at room temperature, treated with water (300 mL) and extracted with Et$_2$O (3×200 mL). The combined organic phases were washed with water (3×300 mL) and dried over sodium sulfate. The solvents were removed to leave an orange oil. Distillation under reduced pressure gave 81.67 g (68.8%) of the title compound as a yellow oil (bp. 140–142° C./0.2 mbar). $^1$H NMR (CDCl$_3$, δ): 7.25–7.11 (m, 3H); 7.01 (td, $^3$J=7.3 Hz, $_4$J=1.4 Hz, 1H); 5.76 (d, $^4$J=0.7 Hz, 1H); 3.29 (s, 2H) 1.77–1.74 (m, 5H); 1.27–1.13 (m, 5H); 0.90 (m, 1H); 0.24 (s, 6H). $^{13}$C NMR (CDCl$_3$, δ): 162.44; 145.24; 136.60; 126.47; 123.07; 122.37; 118.91; 106.32; 39.52; 27.69; 26.77; 26.46; 26.33; −3.55.

EXAMPLE 4
2-(tert-butyldiphenylsiloxy)indene

To a solution of tert-butyldiphenylchlorosilane (42.43 g, 154.4 mmol) and DBU (25.64 g, 168.4 mmol) in benzene (200 mL) was added 2-indanone (18.38 g, 139.1 mmol) in one portion. The reaction mixture was stirred overnight, diluted with Et$_2$O (200 mL), washed with 10% HCl (2×200 mL) and water (2×200 mL) and dried over sodium sulfate. The solvents were evaporated to leave a dark brown oil. Distillation under reduced pressure gave 38.22 g (74.1%) of the title compound as a yellow oil (bp. 172–175° C./0.05 mbar). $^1$H NMR (CDCl$_3$, δ): 7.77–7.74 (m, 4H); 7.46–7.36 (m, 6H) 7.18–7.16 (m, 1H); 7.11–7.07 (m, 1H); 6.98–6.94 (m, 2H); 5.48 (d, $^4$J=0.7 Hz, 1H); 3.29 (s, 2H); 1.09 (s, 9H). $^{13}$C NMR (CDCl$_3$, δ): 162.13; 145.17; 136.75; 135.53; 132.43; 130.20; 127.99; 126.51; 123.15; 122.49; 119.24; 107.91; 39.43; 26.60; 19.46.

EXAMPLE 5
2-(tert-butyldimethylsiloxy)bisbenz[e,g]indene

To a suspension of bisbenz[e,g]-2-indanone (35.90 g, 154.5 mmol) and tertbutyldimethylchlorosilane (28.00 g, 185.5 mmol) in benzene (300 mL) was added dropwise DBU (30.60 g, 201.0 mmol) while keeping the reaction mixture cold with an icebath. Stirring was continued for 1 hour at room temperature. The organic phase was washed with water (200 mL), 5% HCl (2×200 mL), water (200 mL) and dried over sodium sulfate. Evaporation of the solvents left a residue which was washed with MeOH (3×200 mL) to give the title compound (38.35 g, 110.7 mmol, 71.6%) as a slightly pink powder. EIMS (calcd/found): 346.1753/346.1744. $^1$H NMR (CDCl$_3$, δ): 8.72–8.67 (m, 1H); 8.66–8.62 (m, 1H); 8.02–7.96 (m, 1H); 7.82–7.99 (m, 1H); 7.62–7.57 (m, 2H); 7.56–7.50 (mn, 1H); 7.49–7.44 (m, 1H); 6.32 (m, 1H); 3.73 (m, 2H); 1.03 (s, 9H); 0.33 (s, 6H). $^{13}$C NMR (CDCl$_3$, δ): 163.16; 139.79; 130.11; 129.41; 128.34; 127.73; 127.21; 126.67; 126.07; 125.53; 124.42; 123.91; 123.38; 123.24; 122.96; 104.55; 39.81; 25.68; 18.29; −4.50.

EXAMPLE 6
2-(tert-butyldimethylsiloxy)-4,7-dimethylindene

To a solution of tert-butyldimethylchlorosilane (2.85 g, 18.9 mmol) and 4,7-dimethyl-2-indanone (2.53 g, 15.8 mmol, obtained by oxidation of 4,7-dimethylindene) in benzene (30 mL) was added DBU (3.13 g, 20.5 mmol) and the reaction mixture was stirred for 2 hours at room temperature. The mixture was diluted with Et$_2$O (50 mL), washed with water (2×50 mL), 5% HCl (50 mL) water (2×50 mL) and dried over sodium sulphate. Evaporation of the solvents left a dark oil that was dissolved in pentane (30 mL). The unreacted starting materials were crystallized at −15° C. and removed by filtration. Evaporation of the solvent gave 3.03 g (69.9%) of fairly pure title compound as an orange oil. $^1$H NMR (CDCl$_3$, δ): 6.94 (dq, $^3$J=7.7 Hz, $^4$J=0.3 Hz, 1H),; 6.78 (dq, $^3$J=7.7 Hz, $^4$J=0.3 Hz, 1H); 5.84 (t, $^4$J=1.1 Hz, 1H); 3.20 (m, 2H); 2.30 (s, 3H); 2.25 (s, 3H); 1.00 (s, 9H); 0.27 (s, 6H); $^{13}$C NMR (CDCl$_3$, δ): 162.08; 143.39; 134.89; 129.45; 127.78; 125.49; 123.84; 105.28; 38.80; 25.65; 18.29; 18.21; −4.57.

EXAMPLE 7
Bis(2-(tert-butyldimethylsiloxy)indenyl)ethane

To a solution of 2-(tert-butyldimethylsiloxy)indene (36.96 g, 150.0 mmol) in THF (150 mL) at 0° C. was added dropwise n-BuLi (60.0 mL of a 2.5 M solution in hexanes, 150.0 mmol) and the reaction mixture was stirred overnight at room temperature. The resulting solution was then cooled to −80° C. and treated dropwise with a solution of dibromoethane (14.09 g, 75.0 mmol) in THF (50 mL). After completed addition the reaction mixture was stirred overnight at room temperature and washed with saturated ammonium chloride solution (300 mL). Solvents from the organic phase were evaporated and the product was dissolved in Et$_2$O (300 mL), washed with water (2×200 mL) and dried over sodium sulphate. Repeated crystallizations at −15° C. afforded 22.54 g (57.9%) of the title compound as an off-white solid. The first crystalline fraction consisted of diastereomerically pure material (Mp 108–110° C.). EIMS (calcd/found): 518.3036/518.3028. $^1$H NMR (CDCl$_3$, δ, major diastereomer): 7.18–7.07 (m, 6H); 6.97 (td, $^3J$=7.4 Hz, $^4J$=1.3 Hz, 2H); 5.66 (s, 2H); 3.17 (m, 2H); 1.89–1.84 (m, AA', 2H); 1.59–1.54 (m, BB', 2H); 0.94 (s, 18H); 0.23 (s, 6H); 0.21 (s, 6H). $^{13}$C NMR (CDCl$_3$, δ, major diastereomer): 164.96; 144.39; 140.62; 126.50; 122.58; 122.41; 118.74; 104.97; 49.18; 25.67; 24.34; 18.12; –4.68; –4.88. $^1$H NMR (CDCl$_3$, δ, minor diastereomer): 7.17–7.05 (m, 6H); 6.97 (td, $^3J$=7.4 Hz, $^4J$=1.2 Hz, 2H); 5.63 (s, 2H); 3.21 (m, 2H); 1.76–1.75 (m, 4H); 0.94 (s, 18H); 0.22 (s, 6H); 0.20 (s, 6H). $^{13}$C NMR (CDCl$_3$, δ, minor diastereomer): 165.18; 144.35; 140.68; 126.53; 122.71; 122.35; 118.74; 104.87; 49.04; 25.67; 25.30; 18.14; –4.77.

EXAMPLE 8
Bis(2-(t-hexyldimethylsiloxy)indenyl)ethane

To a solution of 2-(t-hexyldimethylsiloxy)indene (68.62 g, 250.0 mmol) in THF (250 mL) at 0° C. was added dropwise n-BuLi (100.0 mL of a 2.5 M solution in hexanes, 250.0 mmol), and the reaction mixture was stirred overnight at room temperature. The resulting solution was then cooled to –80° C. and treated dropwise with a solution of dibromoethane (23.48 g, 125.0 mmol) in THF (100 mL). After completed addition the reaction mixture was stirred overnight at room temperature and washed with saturated ammonium chloride solution (350 mL). Solvents from the organic phase were evaporated, and the product was dissolved in Et$_2$O (350 mL), washed with water (2×300 mL) and dried over sodium sulphate. Repeated crystallizations at –15° C. afforded 37.48 g (52.2%) of the title compound as off-white crystals. The first crystalline fraction consisted of diastereomerically pure material that was used for spectral characterization. EIMS (calcd/found): m/e 574.3662/574.3659. $^1$H NMR (CDCl$_3$, δ): 7.22–7.07 (m, 6H); 6.97 (td, $^3J$=7.4 Hz, $^4J$=1.2 Hz, 2H); 5.65 (s, 2H); 3.15 (m, 2H); 1.91–1.84 (m, AA', 2H); 1.67 (sept, $^3J$=6.8 Hz, 2H); 1.57–1.50 (m, BB', 2H); 0.89 (m, 24H); 0.27 (s, 6H); 0.24 (s, 6H). $^{13}$C NMR (CDCl$_3$, δ): 164.75; 144.45; 140.58; 126.46; 122.60; 122.33; 118.68; 104.96; 49.24; 33.93; 25.03; 24.32; 20.14; 20.02; 18.51; 18.47; –2.66; –2.95.

EXAMPLE 9
Bis(2-(cyclohexyldimethylsiloxy)indenyl)ethane

To an ice-cooled solution of 2-(cyclohexyldimethylsiloxy)indene (13.62 g, 50.0 mmol) in THF (50 mL) was added dropwise n-BuLi (20.0 mL of a 2.5 M solution in hexanes, 50.0 mmol) and the reaction mixture was stirred overnight at room temperature. The resulting solution was then cooled to –80° C. and treated dropwise with a solution of dibromoethane (4.70 g, 25.0 mmol) in THF (30 mL). The reaction mixture was gradually warmed to room temperature, stirred overnight and washed with saturated ammonium chloride solution (150 mL). The organic phase was dried over sodium sulfate. Solvents were evaporated and the remaining oil was dissolved in Et$_2$O (100 mL). Repeated crystallizations gave a total yield 4.03 g (28.2%) of the title compound as off-white crystals. The first crystalline fraction was used for spectral characterization. EIMS (calcd/found): m/e 570.3349/570.3342. $^1$H NMR (CDCl$_3$, δ): 7.19–7.07 (m, 6H); 6.99 (td, $^3J$=7.3 Hz, $^4J$=1.3 Hz, 2H); 5.65 (s, 2H); 3.17 (m, 2H); 1.84–1.79 (m, AA', 2H); 1.73 (m, 10H); 1.59–1.54 (m, BB', 2H); 1.20 (m, 10H); 0.84 (m, 2H); 0.22 (s, 6H); 0.22 (s, 6H). $^{13}$C NMR (CDCl$_3$, δ): 164.98; 144.47; 140.65; 126.51; 122.52; 122.33; 118.72; 104.64; 49.09; 27.72; 26.80; 26.48; 26.37; 24.29; –3.60.

EXAMPLE 10
Bis(2-(tert-butyldiphenylsiloxy)indenyl)ethane

To a solution of 2-(tert-butyldiphenylsiloxy)indene (32.6 g, 88.0 mmol) in THF (200 mL) at 0° C. was added dropwise n-BuLi (35.5 mL of a 2.5 M solution in hexane, 88.8 mmol), and the reaction mixture was stirred overnight at room temperature. The resulting solution was then cooled to –80° C. and treated dropwise with a solution of dibromoethane (8.26 g, 44.0 mmol) in THF (50 mL). The reaction mixture was gradually warmed to room temperature, stirred overnight and washed with saturated ammonium chloride solution (2×300 mL). The organic phase was dried over sodium sulfate. Evaporation of the solvents left a brown oil that was dissolved in boiling Et$_2$O (300 mL). Cooling to –15° C. gave 13.7 g (40.7%) of the title compound as a diastereomerically pure white microcrystalline powder. EIMS (calcd/found): m/e 766.3662/766.3641. $^1$H NMR (CDCl$_3$, δ): 7.78–7.75 (m, 4H); 7.71–7.68 (m, 4H); 7.48–7.33 (m, 12H); 7.22–7.20 (m, 2H); 7.09–7.05 (m, 2H); 6.93–6.88 (m, 4H); 5.28 (s, 2H); 3.36 (m, 2H); 2.21–2.15 (m, AA', 2H); 1.85–1.79 (m, BB', 2H); 1.06 (s, 18H). $^{13}$C NMR (CDCl$_3$, δ): 164.06; 144.19; 140.54; 135.45; 132.28; 131.91; 130.06; 129.99; 127.84; 127.79; 126.45; 122.65; 122.54; 119.06; 106.81; 49.25; 26.61; 25.10; 19.38. The mother liquor was evaporated to dryness and dissolved in boiling pentane (150 mL). Concentration and cooling to –15° C. gave the second crop 1.62 g (4.8%) of the title compound as a brown powder enriched in the minor diastereomer (total yield 45.5%).

EXAMPLE 11
Bis(2-(tert-butyldimethylsiloxy)bisbenz[e,g]indenyl)ethane

To an ice-cooled solution of 2-(tert-butyldimethylsiloxy) bisbenz[e,g]indene (20.00 g, 63,48 mmol) in THF (80 mL) was added dropwise n-BuLi (25.4 mL of a 2.5 M solution in hexanes, 63.50 mmol) and the reaction mixture stirred at room temperature for 1 hour. The solvents were removed in vacuo and toluene (200 mL) was added. The resulting solution was cooled to –80° C. and dibromoethane (5.95 g, 31.67 mmol) in toluene (20 mL) was added dropwise. The reaction mixture was gradually warmed to room temperature, stirred overnight and washed with saturated ammonium chloride solution (2×100 mL). The organic phase was dried over sodium sulfate. Concentration and cooling to –15° C. gave the title compound (900 mg, 1.25 mmol, 3.9%) as an off-white solid. EIMS (calcd/found): m/e 718.3662/718.3659. $^1$H NMR (CDCl$_3$, δ): 8.73–8.69 (m, 2H); 8.66 (dt, $^3J$=8.2 Hz, $^4J$=0.6 Hz, 2H); 8.02–7.98 (m, 2H); 7.63–7.58 (m, 6H); 7.42 (ddd, $^3J$=8.2 Hz, $^3J$=6.9 Hz, $^4J$=1.3 Hz, 2H); 7.34 (ddd, $^3J$=8.2 Hz, $^3J$=6.9 Hz, $^4J$=1.2 Hz, 2H); 6.17 (d, $^4J$=0.4 Hz, 2H); 3.57–3.54 (m, 2H); 2.09–2.06 (m, 2H); 1.76–1.73 (m, 2H); 0.72 (s, 18H); 0.11 (s, 6H); 0.03 (s, 6H). $^{13}$C NMR (CDCl$_3$, δ); 166.68; 139.37; 131.67; 130.32; 129.25; 127.93; 127.04; 126.70; 125.91; 125.46; 124.54; 123.61; 123.43; 123.20; 122.97; 102.67; 49.93; 25.48; 23.68; 18.04; –4.82; –5.03.

EXAMPLE 12
Bis(1-(trimethylsilyl)-2-(tert-butyldimethylsiloxy)-3-indenyl)ethane To a solution of bis(2-(tert-butyldimethylsiloxy)indenyl) ethane (10.38 g, 20.0 mmol) in THF (100 mL) at –20° C. was added dropwise n-BuLi (16.1 mL of a 2.5 M solution in hexane, 40.2 mmol) and the reaction mixture was stirred for 3 hours at room temperature. To the resulting solution was added dropwise chlorotrimethylsilane (6.85 g, 63.0 mmol, 8.0 mL) at 0° C. After completed addition the reaction mixture was stirred overnight at room temperature and the solvents were evaporated. The remaining orange solid was extracted with CH$_2$Cl$_2$ and filtrated through celite. The solvent was evaporated and the product was dissolved in Et$_2$O (150 mL). Concentration and cooling to 0° C. gave 10.29 g (77.6%) of a 2:1 diastereomeric mixture of the title compound as off-white crystals. EIMS (calcd/found): m/e 662.3827/662.3834. $^1$H NMR (CD$_2$Cl$_2$, δ, major/minor diastereomer): 7.51–7.49 (m, 2H, major); 7.42–7.40 (m, 2H, minor); 7.29–7.24 (m, 4+2H, major/minor); 7.22–7.17 (m, 2H, minor); 7.08–7.02 (m, 2+2H, major/minor); 3.29 (s, 1H, minor); 3.27 (s, 1H, major); 3.00–2.96 (m, AA', 2H, minor); 2.72–2.65 (m, AA'BB', 4H, major); 2.44–2.40 (m, BB', 2H, minor); 1.02 (s, 18H, major); 1.01 (s, 18H, minor); 0.20 (s, 6H, minor); 0.19 (s, 6H, major); 0.10 (s, 6H, minor); 0.05 (s, 6H, major); 0.02 (s, 18H, minor); 0.01 (s, 18H, major). $^{13}$C NMR (CD$_2$Cl$_2$, δ, major diastereomer): 158.32; 144.56; 139.24; 125.09; 122.74; 121.98; 119.89; 118.08; 45.08; 26.14; 24.06; 18.52; –2.39; –3.40; –4.66. $^{13}$C NMR (CDCl$_3$, δ, minor diastereomer): 158.08; 144.50; 139.14; 124.97; 122.62; 121.95; 119.95; 118.50; 45.13; 26.14; 23.86; 18.47; –2.29; –3.40; –4.24.

EXAMPLE 13
Dimethylbis(2-(tert-butyldimethylsiloxy)indenyl)silane

To a solution of 2-(tert-butyldimethylsiloxy)indene (12.32 g, 50.0 mmol) in Et$_2$O (50 mL) at 0° C. was added dropwise n-BuLi (20.0 mL of a 2.5 M solution in hexane, 50.0 mmol) and the reaction mixture was stirred overnight at room temperature. The resulting solution was then added dropwise to a solution of dimethyldichlorosilane (3.03 mL, 25.0 mmol) in Et$_2$O (25 mL) at 0° C. The reaction mixture was stirred overnight at room temperature and washed with saturated ammonium chloride solution (150 mL), water (3×100 mL) and dried over sodium sulfate. Evaporation of the solvents left a red oil that was dissolved in a 1:1 mixture of MeOH and acetone. Concentration and cooling to –30° C. gave 5.78 g (42.1%) of the title compound as slightly yellow crystals. The first crop consisted exclusively of the racemic diastereomer. EIMS (calcd/found): m/e 548.2962/548.2958. Mp: 92–94° C. $^1$H NMR (CDCl$_3$, δ): 7.22–7.14 (m, 6H); 6.98 (td, $^3$J=7.3 Hz, $^4$J=1.4 Hz, 2H); 5.85 (s, 2H); 3.99 (s, 2H); 0.97 (s, 18H); 0.34 (s, 6H); 0.28 (s, 6H); –0.23 (s, 6H). $^{13}$C NMR (CDCl$_3$, δ): 164.96; 144.44; 137.55; 125.13; 122.75; 121.41; 118.83; 104.00; 43.06; 25.77; 18.20; 4.34; –4.88; –6.99. The oily residue was washed with copiously with cold MeOH (3×50 mL), cold pentane (50 mL) and dried in vacuo to yield 3.47 g (24.8%) of the fairly pure meso diastereomer as a red oil (total yield 66.9%).

EXAMPLE 14
Dimethylbis(2-(t-hexyldimethylsiloxy)indenyl)silane

To a solution of 2-(t-hexyldimethylsiloxy)indene (35.58 g, 129.6 mmol) in Et$_2$O (120 mL) at 0° C. was added dropwise n-BuLi (52.4 mL of a 2.5 M solution in hexane, 130.9 mmol) and the reaction mixture was stirred overnight at room temperature. The resulting solution was then added dropwise to a solution of dimethyldichlorosilane (7.9 mL, 64.8 mmol) in Et$_2$O (50 mL) at 0° C. The reaction mixture was stirred overnight at room temperature and washed with saturated ammonium chloride solution (300 mL), water (2×200 mL) and dried over sodium sulfate. Evaporation of the solvents left a red oil that was dissolved in a 4:1 mixture of MeOH and acetone. Concentration and cooling to –30° C. gave 11.67 g (29.7%) of the title compound as a white powder. The crystalline first crop consisted exclusively of the racemic diastereomer. EIMS (calcd/found): m/e 604.3588/604.3585. $^1$H NMR (CDCl$_3$, δ): 7.22–7.13 (m, 6H); 6.98 (td, $^3$J=7.3 Hz, $^4$J=1.4 Hz, 2H); 5.85 (s, 2H); 3.99 (s, 2H); 1.72 (sept, $^3$J=6.9 Hz, 2H); 0.94 (s, 6H); 0.94 (s, 6H); 0.90 (d, $^3$J=6.9 Hz, 6H); 0.89 (d, $^3$J=6.9 Hz, 6H); 0.38 (s, 6H); 0.34 (s, 6H); –0.23 (s, 6H). $^{13}$C NNR (CDCl$_3$, δ): 164.87; 144.49; 137.53; 125.13; 122.86; 121.38; 118.84; 104.26; 43.15; 33.76; 25.19; 20.17; 20.08; 18.54; 18.45; –2.30; –2.75; –6.73. The oily residue was washed with cold MeOH (3×100 mL) and dried in vacuo to yield 14.02 g (35.8%) of the fairly pure meso diastereomer as a red oil (total yield 65.5%).

EXAMPLE 15
[Bis(2-(tert-butyldimethylsiloxy)bisbenz[e,g]indenyl)] zirconium dichloride To a solution of 2-(tert-butyldimethylsiloxy)bisbenz[e,g] indenene (6.83 g, 19.7 mmol) in THF (50 mL) was added dropwise n-BuLi (7.9 mL of a 2.5 M solution in hexanes, 19.7 mmol) at –20° C. The resulting red solution was allowed to warm to room temperature and added via cannula to a solution of ZrCl$_4$ (2.24 g, 9.6 mmol) in THF (50 mL). The reaction mixture was refluxed for 20 h. Evaporation of the THF left a solid that was extracted with CH$_2$Cl$_2$ (50 mL) and filtrated through celite to remove lithium chloride. Evaporation of the CH$_2$Cl$_2$ left a red oily solid which was washed with Et$_2$O (2×50 mL) to leave 2.97 g (34.0%/o) of the title compound as a pale green powder. In the EIMS mass spectrum of the title compound parent ions of composition C$_{46}$H$_{50}$Si$_2$O$_2$ZrCl$_2$$^+$ were observed in the appropriate isotope ratios at m/e=850–859. $^1$H NMR (CDCl$_3$, δ): 8.45 (m, 4H); 7.66 (m, 4H); 7.50–7.41 (m, 8H); 6.24 (s, 4H); 1.08 (s, 18H); 0.34 (s,12H). $^{13}$C NMR (CDCl$_3$, δ): 153.11; 129.88; 129.02; 128.2 1; 128.13; 126.95; 126.82; 124.25; 123.37; 118.32; 97.22; 25.80; 18.48; –4.12.

EXAMPLE 16
rac-[ethylenebis(2-(tert-butyldimethylsiloxy)indenyl)] zirconium dichloride To an ice-cooled solution of bis(2-(tert-butyldimethylsiloxy)indenyl)ethane (5.37 g, 10.3 mmol) in THF (50 mL) was added dropwise n-BuLi (8.3 mL of a 2.5 M solution in hexanes, 20.7 mmol) and the reaction mixture was stirred overnight at room temperature. The resultant off-yellow suspension was then added via cannula to a suspension of ZrCl$_4$ (2.41 g, 10.3 mmol) in THF (20 mL) at –80° C. The reaction mixture was gradually warmed to room temperature and stirred overnight. Evaporation of the solvents left a yellow solid that was extracted with CH$_2$Cl$_2$ (150 mL) and filtrated through celite to remove lithium chloride. Concentration and cooling to –30° C. gave 1.47 g (21.0%) of the title compound as a yellow microcrystalline solid. In the EIMS mass spectrum of the title compound parent ions of composition C$_{32}$H$_{44}$Si$_2$O$_2$ZrCl$_2$$^+$ were observed in the appropriate isotope ratios at m/e=676–684. $^1$H NMR (CD$_2$Cl$_2$, δ): 7.64 (dq, J=8.6 Hz, 1.9 Hz, 0.9 Hz, 2H); 7.31–7.27 (m, 4H); 7.07–7.03 (m, 2H); 5.93 (d, J=0.8 Hz, 2H); 4.01–3.90 (m, AA', 2H); 3.58–3.47 (m, BB', 2H); 1.00 (s, 18H); 0.20 (s, 6H); 0.19 (s, 6H). $^{13}$C NMR (CD$_2$Cl$_2$, δ): 150.12; 126.17; 125.14; 124.86; 124.79; 123.35; 116.99; 108.54; 98.61; 26.30; 25.80; 18.61; –3.94; –4.27.

EXAMPLE 17
rac-[Ethylenebis(2-(tert-butyldimethylsiloxy)-4,5,6,7-tetrahydroindenyl]zirconium dichloride A mixture of rac-[Ethylenebis((2-tert-butyldimethylsiloxy)indenyl)]zirconium dichloride (1.00 g, 1.47 mmol) and PtO$_2$ (20 mg) in CH$_2$Cl$_2$ (150 mL) was hydrogenated at 70 bar in a stirred reactor for 16 h. The light green suspension was filtered through Celite and the solvent evaporated. The residue was dissolved in hexane (50 mL) and cooled to 0° C. to provide 0.80 g (79.2%) of the title compound as a light green microcrystalline solid. In the EIMS mass spectrum of the title compound parent ions of composition C$_{32}$H$_{52}$Si$_2$O$_2$ZrCl$_2$$^+$ were observed at m/e= 684–692 in the appropriate isotope ratios. $^1$H NMR (CD$_2$Cl$_2$, δ): 5.69 (s, 2H); 3.39–3.29 (m, AA', 2H); 3.04–2.97 (m, 2H); 2.85–2.77 (m, 2H); 2.73–2.64 (m, BB', 2H); 2.48–2.34 (m, 4H); 1.90–1.70 (m, 4H); 1.59–1.42 (m, 4H); 0.92 (s, 18H); 0.20 (s, 6H); 0.16 (s, 6H). $^{13}$C NMR (CD$_2$Cl$_2$, δ): 142.24; 127.66; 11 7.29; 114.18; 106.45; 25.46; 24.46; 23.80; 22.05; 21.92; 21.75; 18.10; –4.09; –4.65.

EXAMPLE 18
rac-ethylenebis(2-tert-butyldimethylsiloxy-1-indenyl) hafnium dichloride To a solution of bis(2-(tert-butyldimethylsiloxy)indenyl) ethane (10.38 g, 20.0 mmol) in THF (80 mL) at 0° C. was added dropwise n-BuLi (16.1 mL of a 2.5 M solution in hexane, 40.2 mmol) and the reaction mixture was stirred overnight at room temperature. The solvents were removed in vacuo and the resulting off-white powder was mixed with $HfCl_4$ (6.41 g, 20.0 mmol). The mixture was cooled to −80° C. and precooled $CH_2Cl_2$ (150 mL) was added. The light yellow suspension was gradually warmed to room temperature, stirred overnight and filtrated through celite to remove lithium chloride. Concentration and cooling to −30° C. gave 1.96 g (12.8%) of the title compound as a light yellow microcrystalline solid. In the EIMS mass spectrum of the title compound, parent ions of composition $C_{32}H_{44}Si_2O_2HfCl_2^+$ were observed in the appropriate isotope ratios at m/e=760–774. $^1$H NMR ($CD_2Cl_2$, δ): 7.64 (dq, J=8.5 Hz, 1.8 Hz, 1.0 Hz, 2H); 7.34–7.25 (m, 4H); 7.05–7.01 (m, 2H); 5.86 (d, $^4$J=0.7 Hz, 2H); 4.02–3.92 (AA', 2H); 3.71–3.61 (BB', 2H); 1.02 (s, 18H); 0.22 (s, 6H); 0.21 (s, 6H). $^{13}$C NMR ($CD_2Cl_2$, δ): 148.64; 126.19; 124.97; 124.35; 124.30; 123.49; 115.47; 105.37; 96.46; 25.84; 25.52; 18.62; −3.92; −4.26.

EXAMPLE 19
rac-[Ethylenebis(2-(t-hexyldimethylsiloxy)indenyl)]zirconium dichloride To an ice-cooled solution of bis(2-(t-hexyldimethylsiloxy)indenyl)ethane (11.50 g, 20.0 mmol) in THF (100 mL) was added dropwise n-BuLi (16.0 mL of a 2.5 M solution in hexane, 40.0 mmol) and the reaction mixture was stirred overnight at room temperature. The resultant off-yellow suspension was then added via cannula to a suspension of $ZrCl_4$ (4.66 g, 20.0 mmol) in THF (25 mL) at −80° C. The reaction mixture was gradually warmed to room temperature and stirred overnight. Evaporation of the solvents left a yellow solid that was extracted with $CH_2Cl_2$ (150 mL) and filtrated through Celite to remove lithium chloride. Concentration and cooling to −30° C. gave 3.25 g (22.1%) of the title compound as a yellow microcrystalline solid. Single crystals for X-ray diffraction were obtained from a saturated toluene solution at ambient temperature. In the EIMS mass spectrum of the title compound parent ions of composition $C_{36}H_{52}Si_2O_2ZrCl_2^+$ were observed in the appropriate isotope ratios at m/e=732–740. $^1$H NMR ($CD_2Cl_2$, δ): 7.66 (dq, J=8.6 Hz, 1.8 Hz, 1.0 Hz, 2H); 7.35–7.29 (m, 4H); 7.08–7.04 (m, 2H); 5.95 (d, $^4$J=0.6 Hz, 2H); 4.04–3.94 (m, AA', 2H); 3.56–3.46 (m, BB', 2H); 1.74 (sept. $^3$J=6.8 Hz, 2H); 0.99 (s, 6H); 0.97 (s, 6H); 0.95 (d, $^3$J=6.8 Hz, 6H); 0.94 (d, $^3$J=6.8 Hz, 6H); 0.26 (s, 6H); 0.25 (s, 6H). $^{13}$C NMR ($CD_2Cl_2$, δ): 150.48; 126.13; 125.18; 125.10; 124.85; 123.32; 116.94; 98.53; 34.22; 26.41; 25.84; 20.35; 20.14; 18.80; 18.64; −1.62; −2.01.

EXAMPLE 20
rac- and meso-[dimethylsilylenebis(2-(tert-butyldimethylsiloxy)indenyl)]zirconium dichlorides To a solution of dimethylbis(2-(tert-butyldimethylsiloxy)indenyl)silane (10.98 g, 20.0 mmol) in $Et_2O$ (40 mL) at 0° C. was added dropwise n-BuLi (16.0 mL of a 2.5 M solution in hexane, 40.0 mmol) and the reaction mixture was stirred overnight at room temperature. The solvents were removed in vacuo to leave an off-white powder that was mixed with $ZrCl_4$ (4.66 g, 20 mmol). The mixture was cooled to −80° C. and precooled $CH_2Cl_2$ (150 mL) was added. The light yellow suspension was gradually warmed to room temperature, stirred overnight and filtrated through celite to remove lithium chloride. Concentration and cooling to −30° C. gave 7.95 g (56.0%) of an approximately 2:1 rac/meso mixture of the fairly pure title compound as a bright yellow powder. In the EIMS mass spectrum of the title compound, parent ions of composition $C_{32}H_{46}Si_3O_2ZrCl_2^+$ were observed in the appropriate isotope ratios at m/e=706–714. Small amounts of the fairly pure rac diastereomer of the title compound were obtained by carrying out the reaction in THF solution, followed by removal of LiCl and crystallization from $Et_2O$. 1H NMR ($CD_2Cl_2$, δ, rac): 7.47–7.44 (m, 2H); 7.37–7.27 (m, 4H); 6.91–6.87 (m, 2H); 6.22 (d, $^4$J=0.8 Hz, 2H); 1.19 (s,6H); 0.92 (s, 18H); 0.27 (s, 6H); 0.21 (s, 6H). $^{13}$C NMR ($CD_2Cl_2$, δ, rac): 155.89; 128.69; 127.13; 126.84; 125.07; 124.94; 119.69; 104.50; 73.22; 26.12; 19.23; 1.04; −3.36; −3.87.

Polymerization Tests

EXAMPLE 21

The polymerizations were performed in a 0.5 L Büchi glass autoclave in 200 mL of toluene. In a typical run half of the MAO/toluene solution was added to the reactor and stirred for 5 minutes in order to reduce any impurities in the reactor. In a parallel procedure 10–15 μmmol of the metallocene was dissolved in the remaining half of the MAO/toluene solution and preactivated at 25° C. for 5 min. The catalyst/activator mixture was charged into the reactor and the polymerization was started by introducing the olefin monomer. The polymerization was interrupted after 20 or 60 minutes by addition of ethanol or methanol. The polymer was analyzed after being washed with ethanol/HCl or methanol/HCl.

Methylaluminoxane (MAO) was used as 29.3 w-% toluene solution (Al total 13.1% w/w, Al as TMA 3.50% w/w). High purity ethylene and propylene (99,5%) were used as monomers.

The results are presented in the Table 1 below.

TABLE 1

| Cat. ex. | Polymn. Temperature | Pressure bar | Al:Zr | Activity kgPP/mol | Mw | Mw/Mn |
|---|---|---|---|---|---|---|
| 1 *) | 0 | 1.30 | 3000:1 | 500 | 33100 | 1.9 |
| 1 | 20 | 2.00 | 3000:1 | 5300 | 19000 | 2.4 |
| 1 | 40 | 2.70 | 3000:1 | 9000 | 9200 | 2.7 |
| 1 | 60 | 3.40 | 3000:1 | 7000 | 7000 | 2.9 |
| 1 | 80 | 4.10 | 3000:1 | 3500 | 3400 | 2.6 |
| 1 | 40 | 2.70 | 50:1 | 200 | 27700 | 1.8 |
| 1 | 40 | 2.70 | 250:1 | 8500 | 17700 | 2.1 |
| 1 | 40 | 2.70 | 500:1 | 9900 | 15900 | 2.2 |
| 1 | 40 | 2.70 | 1000:1 | 9400 | 13500 | 2.4 |
| 1 | 40 | 2.70 | 10000:1 | 10200 | 4600 | 2.3 |
| 2 **) | 20 | 2.00 | 3000:1 | 20 | 123000 | 2.1 |
| 2 | 40 | 2.70 | 3000:1 | 150 | 37800 | 1.8 |
| 2 | 60 | 3.40 | 3000:1 | 500 | 12600 | 1.8 |

*) 1 means the catalyst rac.-[Et-(2-(t-BuMe$_2$SiO)Ind]$_2$ZrCl$_2$
**) 2 means the catalyst rac.-[Et-(2-(t-BuMe$_2$SiO)Ind]$_4$]$_2$ZrCl$_2$

EXAMPLE 22

Propylene was polymerized according to Example 21. The conditions and results are presented in Table 2 below.

TABLE 2

| Metallocene | Activity kgPP/mol Zr/h | Mw g(mol) | Mw/Mn | $T_m$ ° C. |
|---|---|---|---|---|
| rac-Et[2-(t-BuMe$_2$SiO)Ind]$_2$ZrCl$_2$ | 5300 | 19900 | 2.4 | 148 |
| rac-Et[t-hexylMe$_2$SiO)Ind]$_2$ZrCl$_2$ | 2700 | 16100 | 2.1 | 146 |
| rac-Me$_2$Si(IndH$_4$)$_2$ZrCl$_2$ | 2300 | 53200 | 2.0 | 146 |
| rac-Et(IndH$_4$)$_2$ZrCl$_2$ | 800 | 33000 | 2.0 | 138 |

$T_{pol}$=20° C.; p=2.0 bar, polymerization time=60 min; Al:Zr=3000:1

EXAMPLE 23

The polymerizations with the [metallocene]$^+$[B(C$_6$F$_6$)$_4$]$^-$ catalyst system were carried out at −20° C. and 2.0 bar propylene pressure using triethylalumina (TEA) as impurity scavenger. In a typical run 0.3 g of TEA was stirred with 50 mL of toluene followed by the addition of 5 μmol of the metallocene. The cation forming agent (14 μmol) was added via a syringe. The polymerization was interrupted after 60 min by addition of ethanol or methanol. The polymer was analyzed after being washed with ethanol/HCl or methanol/HCl.

The conditions and results are presented in Table 3 below.

TABLE 3

| Metallocene | Activity kg PP/mol M/h | [mm] (%) | [mmmm] (%) |
|---|---|---|---|
| [rac-Et[2-(t-BuMe$_2$SiO)Ind]$_2$ZrMe]$^+$[B(C$_6$F$_5$)$_4$]$^-$ | 7500 | 96.0 | 95.3 |
| [rac-Et(Ind)$_2$ZrMe]$^+$[B(C$_6$F$_5$)$_4$]$^-$ | 4600 | 94.9 | 93.7 |
| [rac-Me$_2$Si(Ind)$_2$ZrMe]$^+$[B(C$_6$F$_5$)$_4$]$^-$ | 4600 | 95.7 | 94.9 |

Temperature=−20° C.; Polymerization time=20 min

EXAMPLE 24

Ethylene was polymerized as above. The results are presented in Table 4 below.

TABLE 4

Ethylene polymerization with Et[IndOSiMe$_2$tBu]$_2$ZrCl$_2$/MAO and Me$_2$Si[IndH$_4$]$_2$ZrCl$_2$/MAO /(reference) catalyst systems in toluene (Al:Zr = 3000:1; monomer pressure = 2 bars)

| Run | Catalyst | Activity k.g PE mol Zr/h | Tp ° C. | M$_w$ | M$_w$/M$_n$ | T$_m$ ° C. | Cryst. % |
|---|---|---|---|---|---|---|---|
| 1 | Et[IndOSiMe$_2$tBu]$_2$ZrCl$_2$ | 6900 | 80 | 14700 | 3.8 | 126 | 65 |
| 2 | Me$_2$Si[IndH$_4$]$_2$ZrCl$_2$ | 6400 | 80 | 55800 | 2,0 | 134 | 69 |

EXAMPLE 25

The polymerizations were performed in a 2.0 L Büchi autoclave in 1300 mL of pentane. A complex solution of ÅBO3 (rac-Et[2-(t-BuMe$_2$SiO)Ind]$_2$ZrCl$_2$) and MAO in toluene, having Al/Zr=200, was introduced into the reactor. The amount of metallocene was 2.5 μmol. After the feeding of the catalyst complex solution, the polymerization reactor was heated to 70° C., polymerization temperature. At the beginning of the reaction, 5 bar of ethylene partial pressure was introduced into the polymerization reactor and the reaction was started. After 30 min of polymerization, the reaction was stopped by closing the ethylene valve and releasing the over-pressure from the reactor.

After 30 min of polymerization, the yield of polymer was 120 g polymer, giving a catalyst activity of 526 kgHD-PE/g.Zr.h.

EXAMPLE 26

The polymerizations were performed in a 2.0 L Büchi autoclave in 1300 mL of pentane. A complex solution of ÅBO3 (rac-Et[2-(t-BuMe$_2$SiO)Ind]$_2$ZrCl$_2$) and MAO in toluene, having Al/Zr=200, was introduced into the reactor. The amount of metallocene was 1.25 μmol. After the feeding of the catalyst complex solution, the polymerization reactor was heated to 70° C., polymerization temperature. At the beginning of the reaction, 5 bar of ethylene partial pressure was introduced into the polymerization reactor and the reaction was started. After 30 min of polymerization, the reaction was stopped by closing the ethylene valve and releasing the over-pressure from the reactor.

After 30 min of polymerization, the yield of polymer was 103 g polymer, giving a catalyst activity of 903 kgHD-PE/g.Zr.h.

EXAMPLE 27

The polymerizations were performed in a 2.0 L Büchi autoclave in 1300 mL of pentane. A complex solution of ÅBO3 (rac-Et[2-(t-BuMe$_2$SiO)Ind]$_2$ZrCl$_2$) and MAO in toluene, having Al/Zr=100, was introduced into the reactor. The amount of metallocene was 0.63 μmol. After the feeding of the catalyst complex solution, the polymerization reactor was heated to 70° C., polymerization temperature. At the beginning of the reaction, 5 bar of ethylene partial pressure was introduced into the polymerization reactor and the reaction was started. After 30 min of polymerization, the reaction was stopped by closing the ethylene valve and releasing the over-pressure from the reactor.

After 30 min of polymerization, the yield of polymer was 96 g polymer, giving a catalyst activity of 1670 kgHD-PE/g.Zr.h.

EXAMPLE 28

The polymerizations were performed in a 2.0 L Büchi autoclave in 1300 mL of pentane. A complex solution of ÅBO3 (rac-Et[2-(t-BuMe$_2$SiO)Ind]$_2$ZrCl$_2$) and MAO in toluene, having Al/Zr=100, was introduced into the reactor. The amount of metallocene was 0.6 μmol. After the feeding of the catalyst complex solution, the polymerization reactor was heated to 70° C., polymerization temperature. At the beginning of the reaction, 5 bar of ethylene partial pressure was introduced into the polymerization reactor and the reaction was started. After 30 min of polymerization, the reaction was stopped by closing the ethylene valve and releasing the over-pressure from the reactor.

After 30 min of polymerization, the yield of polymer was 12 g polymer, giving a catalyst activity of 435 kgHD-PE/g.Zr.h.

EXAMPLE 29

The polymerizations were performed in a 2.0 L Büchi autoclave in 1300 mL of pentane. A complex solution of ÅBO3 (rac-Et[2-(t-BuMe$_2$SiO)Ind]$_2$ZrCl$_2$) and MAO in toluene, having Al/Zr=200, was introduced into the reactor. The amount of metallocene was 0.6 μmol. After the feeding of the catalyst complex solution, the polymerization reactor was heated to 70° C., polymerization temperature. At the beginning of the reaction, 5 bar of ethylene partial pressure was introduced into the polymerization reactor and the reaction was started. After 30 min of polymerization, the reaction was stopped by closing the ethylene valve and releasing the over-pressure from the reactor.

After 30 min of polymerization, the yield of polymer was 27 g polymer, giving a catalyst activity of 936 kgHD-PE/g.Zr.h.

EXAMPLE 30

The polymerizations were performed in a 2.0 L Büchi autoclave in 1300 mL of pentane. A complex solution of ÅBO3 (rac-Et[2-(t-BuMe$_2$SiO)Ind]$_2$ZrCl$_2$) and MAO in toluene, having Al/Zr=500, was introduced into the reactor. The amount of metallocene was 0.6 μmol. After the feeding of the catalyst complex solution, the polymerization reactor was heated to 70° C., polymerization temperature. At the beginning of the reaction, 5 bar of ethylene partial pressure was introduced into the polymerization reactor and the reaction was started. After 30 min of polymerization, the reaction was stopped by closing the ethylene valve and releasing the over-pressure from the reactor.

After 30 min of polymerization, the yield of polymer was 73 g polymer, giving a catalyst activity of 2534 kgHD-PE/g.Zr.h.

Comparative Example 1

The polymerizations were performed in a 2.0 L Büchi autoclave in 1300 mL of pentane. A complex solution of TA2677 (Et[1-Ind]$_2$ZrCl$_2$) and MAO in toluene, having Al/Zr=100, was introduced into the reactor. The amount of metallocene was 0.65 μmol. After the feeding of the catalyst complex solution, the polymerization reactor was heated to 70° C., polymerization temperature. At the beginning of the reaction, 5 bar of ethylene partial pressure was introduced into the polymerization reactor and the reaction was started. After 30 min of polymerization, the reaction was stopped by closing the ethylene valve and releasing the overpressure from the reactor.

After 30 min of polymerization, the yield of polymer was 9 g polymer, giving a catalyst activity of 151 kgHD-PE/g.Zr.h.

Comparative Example 2

The polymerizations were performed in a 2.0 L Büchi autoclave in 1300 mL of pentane. A complex solution of TA2677 (Et[1-Ind]$_2$ZrCl$_2$) and MAO in toluene, having Al/Zr=200, was introduced into the reactor. The amount of metallocene was 0.65 μmol. After the feeding of the catalyst complex solution, the polymerization reactor was heated to 70° C., polymerization temperature. At the beginning of the reaction, 5 bar of ethylene partial pressure was introduced into the polymerization reactor and the reaction was started. After 30 min of polymerization, the reaction was stopped by closing the ethylene valve and releasing the overpressure from the reactor.

After 30 min of polymerization, the yield of polymer was 27 g polymer, giving a catalyst activity of 455 kgHD-PE/g.Zr.h.

Comparative Example 3

The polymerizations were performed in a 2.0 L Büchi autoclave in 1300 mL of pentane. A complex solution of TA2677 (Et[1-Ind]$_2$ZrCl$_2$) and MAO in toluene, having Al/Zr=500, was introduced into the reactor. The amount of metallocene was 0.65 μmol. After the feeding of the catalyst complex solution, the polymerization reactor was heated to 70° C., polymerization temperature. At the beginning of the reaction, 5 bar of ethylene partial pressure was introduced into the polymerization reactor and the reaction was started. After 30 min of polymerization, the reaction was stopped by closing the ethylene valve and releasing the overpressure from the reactor.

After 30 min of polymerization, the yield of polymer was 25 g polymer, giving a catalyst activity of 421 kgHD-PE/g.Zr.h.

Explanations of Chemicals Used in Experiments

ÅBO3

TA2677

Commercial product of Witco

MAO: methylalumoxane 30 w-% solution in toluene, produced by Albemarle

Pentane: polymerization grade ultra pure pentane, H$_2$O and O$_2$<<1.0 ppm

Ethylene: polymerization grade, H$_2$O and O$_2$<<1.0 ppm

The polymerizations 28–30 were compared to the prior art comparative polymerizations 1–3. The results are presented in Table 5.

TABLE 5

Comparison of ÅBO3 and TA2677

| Compound | ÅBO3 | | | | TA2677 | | |
|---|---|---|---|---|---|---|---|
| Concentration | 0.6 | | | | 0.65 | | |
| Al/Zr (mol/mol) | 100 | 200 | 500 | | 100 | 200 | 500 |
| Medium | | | | Pentane | | | |
| Ethylene | | | | 5 bar | | | |
| Temp. ° C. | | | | 70 | | | |
| Yield (g) | 12 | 27 | 73 | | 9 | 27 | 25 |
| Activity kgHD-PE/g · cat · h | 435 | 936 | 2534 | | 151 | 455 | 521 |
| Mw | | 205000 | 114000 | | 101000 | 128000 | 124000 |
| D | | 4.0 | 2.8 | | 2.9 | 3.4 | 2.8 |

Description of Examples

Examples 25 to 27 describe the influence of metallocene concentration on the polymerization. By using too high concentration the metal activity becomes too low. From these examples it can be seen that the metal activity is increased when the amount of the catalyst is decreased from 2.5 μmol down to 0.6 μmol.

Figure 1:
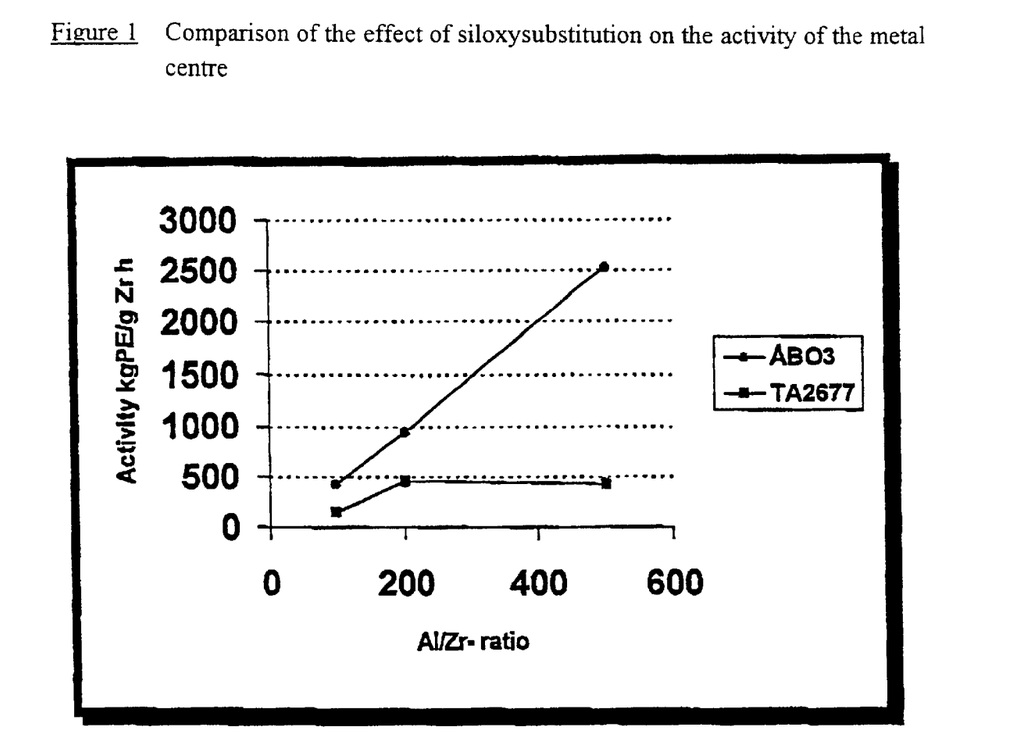
FIG. 1 shows a comparison of the effect of siloxysubstitution on the activity of the metal centre

Examples 28–30 and comparative examples 1–3 shows the importance of a 2-siloxy substituent on catalyst activity. When ethylenebis indenyl zirconium dichloride has a siloxy substituent the catalyst activity is increased especially with low Al/Zr-ratios indicating easy complex formation between metallocene and MAO and also increased activity of the zirconium. The difference can be seen best in FIG. 1 above.

What is claimed is:

1. A precursor for an olefin polymerization catalyst having improved activitvy having the formula (I):

(I)

wherein: each IndY is the same or different and is one of a mono- or polysubstituted, fused or non-fused, homo- or heterocyclic indenyl ligand, dihydroindenyl ligand or tetrahydroindenyl ligand, which ligand is substituted at the 2-position of its indenyl structure by the group Y, which group Y has the following structure (II):

(II)

wherein D is one of silicon or germanium, $R^3$, $R^{3'}$ and $R^4$ are the same or different and are one of a hydrogen atom, a $C_1$–$C_{10}$ hydrocarbyl group or a $C_1$–$C_{10}$ hydrocarbyloxy group, or at least two of $R^3$, $R^{3'}$ and $R^4$ form together a $C_2$–$C_{20}$ ring structure; M is a transition metal of group 4 of the Periodic Table and is bound to the ligand IndY in at least an $θ_5$ bonding mode; each R is the same or different and is one of a hydrogen atom, a halogen atom, a $C_1$–$C_{10}$ hydrocarbyl group, a $C_1$–$C_{10}$ hydrocarbyloxy group, a trihydrocarbyl silyl group or two R form together a $C_2$–$C_{20}$ ring structure; B is a bridge atom or group between two IndY ligands or between one IndY ligand and the transition metal M; m is 1 or 2; o is 0 or 1; and n is 4-m when there is no bridge or B is a bridge atom or group between two IndY ligands, or n is 4-m-o when B is a bridge atom or group between one IndY ligand and the transition metal M.

2. A catalyst precursor having a formula (III):

(III)

where
M is a metal selected from zirconium, titanium or hafnium,
D is an element selected from silicon (Si) or germanium (Ge),
B is a bridge comprising at least one of —(CH$_2$)$_n$, —Si(R$^3$)$_2$— or —Ge(R$^3$)$_2$—, wherein n=1–8,
$R^1$ and $R^2$ are the same or different groups selected from hydrogen, $C_1$–$C_{10}$ alkyl group, $C_1$–$C_{10}$ alkoxy group, $C_6$–$C_{10}$ aryl group, $C_6$–$C_{10}$ aryloxy group, $C_2$–$C_{10}$ alkenyl group, $C_7$–$C_{10}$ arylalkyl group, $C_7$–$C_{10}$ alkylaryl group, $C_8$–$C_{40}$ arylalkenyl group or a halogen atom,
$R^{3'}$, $R^3$–$R^6$ are the same or different group selected from hydrogen, $C_1$–$C_{10}$ alkyl group, $C_1$–$C_{10}$ alkoxy group, $C_6$–$C_{10}$ aryl group, $C_6$–$C_{10}$ aryloxy group, $C_2$–$C_{10}$ alkenyl group, $C_7$–$C_{22}$ arylalkyl group, $C_7$–$C_{22}$ alkylaryl group, $C_8$–$C_{40}$ arylalkenyl group and a halogen atom, $R^{3'}$ and $R^3$-groups can also be connected to each other to form a ring structure and $R^4$ may also be a ring structure.

3. A catalyst precursor according to claim 1 or 2, characterized in that M is zirconium and D is silicon.

4. A catalyst precursor according to claim 2, characterized in that $R^1$ and $R^2$ are the same.

5. A catalyst precursor of claim 1, characterized in that $R^{3'}$ and or $R^3$ is $C_1$–$C_{10}$ alkyl or aryl group and $R^4$ is $C_1$–$C_{10}$ alkyl or aryl group.

6. A catalyst precursor according to claim 2, characterized in that D is Si, B is —CH$_2$CH$_2$—, R=R$^1$=R$^2$ and is chlorine, R$^3$ is CH$_3$ and R$^5$–R$^6$ is aromatic or aromatic or alkyl or hydrogen.

7. A metallocene catalyst system for polymerization of olefins comprising a precusor having the formula (I):

(I)

wherein: each IndY is the same or different and is one of a mono- or polysubstituted, fused or non-fused, homo- or heterocyclic indenyl ligand, dihydroindenyl ligand or tetrahydroindenyl ligand, which ligand is substituted at the 2-position of its indenyl structure by the group Y, which group Y has the following structure (II):

(II)

wherein D is one of silicon or germanium, R$^3$, R$^3$' and R$^4$ are the same or different and are one of a hydrogen atom, a C$_1$–C$_{10}$ hydrocarbyl group or a C$_1$–C$_{10}$ hydrocarbyloxy group, or at least two of R$^3$, R$^3$' and R$^4$ form together a C$_2$–C$_{20}$ ring structure; M is a transition metal of group 4 of the Periodic Table and is bound to the ligand IndY in at least an η$_5$ bonding mode; each R is the same or different and is one of a hydrogen atom, a halogen atom, a C$_1$–C$_{10}$ hydrocarbyl group, a C$_1$–C$_{10}$ hydrocarbyloxy group, a trihydrocarbyl silyl group or two R form together a C$_2$–C$_{20}$ ring structure; B is a bridge atom or group between two IndY ligands or between one IndY ligand and the transition metal M; m is 1 or 2; o is 0 or 1; and n is 4–m when there is no bridge or B is a bridge atom or group between two IndY ligands, or n is 4–m–o when B is a bridge atom or group between one IndY ligand and the transition metal M, and a cocatalyst, wherein said cocatalyst is methylalumoxane (MAO).

8. The precursor for an olefin polymerization catalyst having improved activity of claim 1, wherein D is germanium.

9. A catalyst precursor according to claim 4 characterized in that R$^1$ and R$^2$ are halogen atoms.

10. A catalyst precursor according to claim 9 characterized in that R$^1$ and R$^2$ are chlorine atoms.

11. A catalyst precursor according to claim 5 characterized in that R$^3$' and R$^3$ are methyl groups.

12. A catalyst precursor according to claim 5 characterized in that R$^4$ is selected from the group consisting of a tert-butyl group, a tert-hexyl group, and a cyclohexyl group.

* * * * *

UNITED STATES PATENT AND TRADEMARK OFFICE
CERTIFICATE OF CORRECTION

PATENT NO. : 6,277,778 B1
DATED : August 21, 2001
INVENTOR(S) : Reko Leino et al.

It is certified that error appears in the above-identified patent and that said Letters Patent is hereby corrected as shown below:

<u>Title page,</u>
Item [73], Assignee, change "Borealis A/S, Lyngby (DK)" to -- Borealis Technology OY, Porvoo (FI) --.

Signed and Sealed this

Thirtieth Day of April, 2002

Attest:

Attesting Officer

JAMES E. ROGAN
*Director of the United States Patent and Trademark Office*